United States Patent [19]

Rajakhyaksha

[11] Patent Number: 4,525,199
[45] Date of Patent: Jun. 25, 1985

[54] METHOD OF IMPROVED PEST CONTROL

[75] Inventor: Vithal J. Rajakhyaksha, Mission Viejo, Calif.

[73] Assignee: Nelson Research & Development Co., Irvine, Calif.

[21] Appl. No.: 310,948

[22] Filed: Oct. 13, 1981

Related U.S. Application Data

[63] Continuation-in-part of Ser. No. 260,201, May 4, 1981, abandoned, which is a continuation of Ser. No. 725,490, Oct. 28, 1976, abandoned, which is a continuation-in-part of Ser. No. 588,247, Jun. 19, 1975, Pat. No. 3,989,816.

[51] Int. Cl.$^3$ ............................................. A01N 25/02
[52] U.S. Cl. ........................................ 514/788; 71/79; 71/88; 71/94; 71/95; 424/127; 424/167; 424/244; 424/358; 514/788; 514/946
[58] Field of Search .......... 71/95, 88, 94, 79, DIG. 1, 71/65; 260/239.3 R; 424/167, 358, 244, 127; 546/243

[56] References Cited

U.S. PATENT DOCUMENTS

| | | | |
|---|---|---|---|
| 3,103,509 | 9/1963 | von Schickh | 546/243 |
| 3,268,397 | 8/1966 | Williams | 546/243 |
| 3,977,860 | 8/1976 | Franz | 71/86 |
| 3,988,318 | 10/1976 | Copes et al. | 424/267 |
| 3,988,351 | 10/1976 | Copes et al. | 424/267 |
| 3,989,816 | 11/1976 | Rajadhyksha | 424/59 |
| 4,310,525 | 1/1982 | Nelson | 424/244 |
| 4,311,481 | 1/1982 | Nelson | 8/564 |
| 4,316,893 | 2/1982 | Rajadhyaksha | 424/180 |
| 4,359,334 | 11/1982 | Brown | 71/95 |
| 4,361,436 | 11/1982 | McCarthy et al. | 71/95 |

FOREIGN PATENT DOCUMENTS 859016 12/1952 Fed. Rep. of Germany .
2029832A 3/1979 United Kingdom .

OTHER PUBLICATIONS

Anon., Chem. Abstr., 46852x, vol. 77, (1972).
Hull et al., Chem. Abstr., 69110x, vol. 76, (1972).
Chem. Abstr.–Chem. Substance Index–9th, Collective Index (1978), p. 22902cs.
Takematsu et al., I, Chem. Ab., v. 83, 2325 (1975), II, v. 84, 160605 (1976).
Rutten, Chem. Ab., v. 55, 19150b, (1961).
Aikawa, et al., "Herbicidal Activity of Caprolactam Derivatives", J. Fac. Agr. Kyushu Univ. 20, 75–78, (1976).
Jelinek, et al., "Alkylated ε-Caprolactams," Chem. Abstracts 9602b (1966).

Primary Examiner—Henry R. Jiles
Assistant Examiner—Bernard I. Dentz
Attorney, Agent, or Firm—Knobbe, Martens, Olson & Bear

[57] ABSTRACT

The disclosure describes a method for improved plant pest control comprising contacting a plant or plant pest with a composition comprising an effective amount of a plant pesticide and an effective delivery enhancing amount of compound having the structural formula

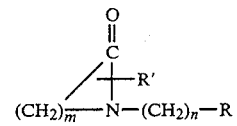

wherein R' is H or a lower alkyl group having 1–4 carbon atoms, m is 3–7, n is 0–17 and R is —CH$_3$,

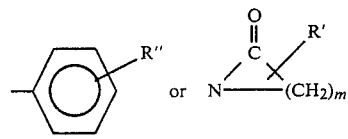

where R" is H or halogen, with the proviso that if m is 3 and R is CH$_3$, then n is 5–17.

Typical plant pesticides include insecticides, fungicides, herbicides, rodenticides, nematicides molluscicides and acaricides. The preferred penetration enhancing compound is 1-n-dodecylaza cycloheptan-2-one.

15 Claims, No Drawings

METHOD OF IMPROVED PEST CONTROL

REFERENCE TO EARLIER FILED APPLICATION

This application is a continuation-in-part of U.S. application Ser. No. 260,201, filed May 4, 1981, now abandoned, which in turn is a continuation of U.S. application Ser. No. 725,490 filed Oct. 28, 1976, now abandoned, which in turn is a continuation-in-part of U.S. application Ser. No. 588,247 filed June 19, 1975, now U.S. Pat. No. 3,989,816.

BACKGROUND OF THE INVENTION

1. Field of the Invention

The present invention generally relates to a method of treatment of plants. More particularly, the invention relates to an improved method of plant pest control.

2. Background of the Prior Art

Pesticides are chemicals designed to combat the attacks of various pests on agricultural and horticultural crops. They fall into three major classes: insecticides, fungicides and herbicides (or weed killers). There are also rodenticides (for control of vertebrate pests), nematicides (to kill microscopic eelworms), molluscicides (to kill slugs and snails) and acaricides (to kill mites).

Pesticides may also be divided into two main types, namely contact or nonsystemic pesticides and systemic pesticides. Contact or surface pesticides do not appreciably penetrate plant tissues and are consequently not transported or translocated, within the plant vascular system. The earlier insecticides, fungicides and herbicides were of this type; their disadvantages are that they are susceptible to the effects of weathering (wind, rain and sunlight) over long periods and new plant growth will be left unprotected and hence open to attack by insect and fungal pests. The early agricultural fungicides were, therefore, protectant fungicides—in other words they are designed to prevent the development of the fungal spores, but once the fungus has become established and infection starts to ramify through the plant tissues such nonsystemic fungicides possess little eradicant action and usually cannot halt the infection.

In contrast, many of the more recent pesticides are systemic in character—these can effectively penetrate the plant cuticle and move through the plant vascular system. Examples are provided by the phenoxyacetic acid selective herbicides, certain organophosphorus insecticides and the more recently discovered systemic fungicides like benomyl.

Systemic fungicides are also sometimes termed plant chemotherapeutants and can not only protect the plant from fungal attack, but also cure or inhibit an established infection. They are little affected by weathering and will also confer immunity on all new plant growth.

Pests can be divided into various groups. In the plant kingdom, characterized by the ability of the organism to photosynthesize carbohydrates from air and water with the aid of the green pigment chlorophyll, higher plants growing where man does not want them are termed weeds and are important pests. Of the lower plants, algae are not generally of as great importance as pests, although in some circumstances, e.g., in lakes and other slow moving water, excessive algal growth or "bloom" may cause considerable damage and require treatment with chemicals (algicides).

Fungi or nonphotosynthetic plants cannot obtain their nutrients from air and water since they do not have chlorophyll; consequently they feed directly on decaying plant or animal matter (saprophytic fungi) or on living plants or animals (parasitic fungi). There are thousands of different species of fungi mainly found in soil—some, like yeasts, are unicellular while others are composed of a network of branched filaments (hyphae). A number of fungi are serious pests attacking both living crop plants and also crops in storage.

Several bacteria are causal agents of plant diseases, although they are not nearly as important as the phytopathogenic fungi. Bacteria can be observed under the microscope and can be classified according to their shape; thus a spherical bacterium is termed a coccus while a rod-shaped one is a bacillus.

Viruses, like bacteria and fungi, attack plants and animals and some species cause significant plant diseases. Viruses form a distinct category of living organism because they are not true cells. Unlike bacteria they are too small (100–300 A) in diameter to be observed with an ordinary microscope, but they can be revealed under the electron microscope—each virus consists of a single strand of DNA or RNA surrounded by a protective coat of protein.

Several higher animals (vertebrates) are important pests, e.g., mice, rats and rabbits; another group of pests is represented by the true insects (arthropods) which are invertebrates. The latter possess three pairs of legs and the adult body has three parts; the arachnids (mites and ticks) differ from true insects in having no distinct division of the body into three parts; also they usually have four pairs of legs. In the lower orders of animals, certain nematodes, parasitic worms often with unsegmented bodies, are important crop pests.

If pesticides are to be active they must reach the ultimate site of action within the target organism. Thus even surface fungicides, like Bordeaux mixture, must be able to penetrate the fungal spore; similarly contact insecticides have to penetrate the insect cuticle, and contact herbicides the plant cuticle when they impinge on it. The requirements if the pesticides are to be systemic in action are much more stringent because in addition they must have the capacity to be absorbed by the roots or leaves or seeds of plants and be delivered to other parts of the plant. In this way the whole plant, including new growth, is protected from fungal attack, or rendered poisonous to any insect that eats or sucks it.

SUMMARY OF THE INVENTION

I have now discovered an improved method of plant pest control by enhancing the delivery of pesticides to plant pests. The foregoing is accomplished through the use of a compound which, when combined with a pesticide, enhances the delivery of the pesticide to plant pests. The composition containing the delivery-enhancing compound and pesticide may be applied directly to the plant pest by topical application or indirectly by topical application to the plants to be protected. The latter indirect method of application enables the pesticide to reach its ultimate site of action, namely the plant pest, after the plant pest has come in contact with the treated plant.

The invention, therefore, relates to an improved method of plant pest control comprising contacting a plant or plant pest with a composition comprising an effective amount of a plant pesticide and an effective, delivery-enhancing amount of a compound having the structural formula

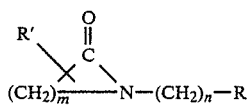

Where R' is H or a lower alkyl group having 1-4 carbon atoms, m is 3-7, n is 0-17, and R is —CH$_3$,

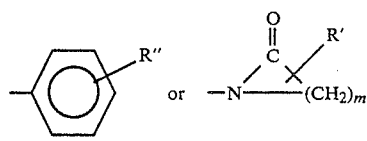

where R" is H or Halogen and R' has the same meaning as above.

In one preferred embodiment, R' is H, m is 5-7, R is CH$_3$ and n is 0-11. The preferred compound is 1-n-dodecylazacycloheptan-2-one.

DETAILED DESCRIPTION OF THE INVENTION

The 1-substituted azacycloalkan-2-ones used in this invention are made by methods described below and as further described in the Examples. Typical examples of compound included in the foregoing formula are the following:

1-n-hexylazacyclopentan-2-one
1-n-heptylazacyclopentan-2-one
1-n-octylazacyclopentan-2-one
1-n-nonylazacyclopentan-2-one
1-n-decylazacyclopentan-2-one
1-n-dodecylazacyclopentan-2-one
1-methylazacycloheptan-2-one
1-n-propylazacycloheptan-2-one
1-n-butylazacycloheptan-2-one
1-n-pentylazacycloheptan-2-one
1-n-hexylazacycloheptan-2-one
1-n-heptylazacycloheptan-2-one
1-n-octylazacycloheptan-2-one
1-n-nonylazacycloheptan-2-one
1-n-decylazacycloheptan-2-one
1-n-dodecylazacycloheptan-2-one
1-n-butylazacyclononan-2-one
1-n-octylazacyclononan-2-one
1-phenylazacyclopentan-2-one
1-benzylazacyclopentan-2-one
1-(2-chlorophenyl)azacyclopentan-2-one
1,3-Bis-(1-azacyclopentan-2-onyl)propane
1,6-Bis-(1-azacyclopentan-2-onyl)hexane The compounds covered by the general formula may be prepared by treating an azacycloalkan-2-one with an alkyl or aralkyl halide or mesylate in the presence of a base, e.g., sodium hydride. The reaction is carried out under anhydrous conditions in a hydrocarbon solvent, for example, dry toluene at reflux temperature for about 10 to 72 hours in an inert atmosphere, for example, nitrogen. This method is outlined below:

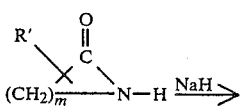

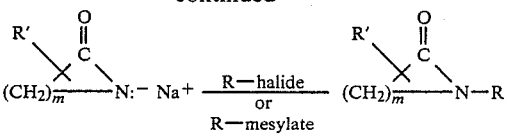

In the above method, substitution of an equimolar ratio of a dibromoalkane in place of an alkyl halide gives Bis-N-azacycloalkan-2-onyl alkane.

Alternatively, a lactone of an alkanoic acid may be heated with an alkyl, aryl or aralkyl amine (with or without solvent) for about 20 to 72 hours at about 180°-250° C. with removal of water to obtain the corresponding 1-substituted azacycloalkan-2-one as shown below:

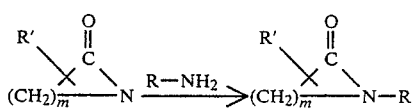

Similarly, heating a lactone of an alkanoic acid with a diaminoalkane in a 2.5 to 1 molar ratio gives the Bis-N-azacycloalkan-2-onyl alkane.

In another method gamma-dialkylaminobutyric acid may be treated with phosphorous trihalide and the resulting acid halide (which need not be isolated) is heated, resulting specifically in the formation of N-alkylazacyclopentan-2-one. Suitable acid halide forming agents include phosphorous trichloride, phosphorous tribromide, thionyl chloride, etc. The acid halide is formed at room temperature and then the reaction temperature is raised to 70°-90° C. One of the alkyl groups on the amino nitrogen of the parent acid is eliminated as alkyl halide. If the alkyl groups on the amino nitrogen are different, the smaller of the two alkyl groups is eliminated preferentially. This method is described below.

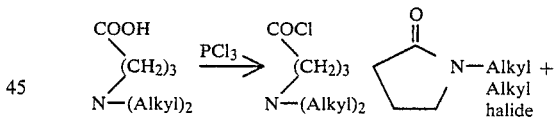

Typical plant pesticides include conventitonal pesticides, including, but not limited to, insecticides, fungicides, herbicides, rodenticides, nematicides, molluscicides, acaricides, plant growth regulators, fumigants, antifeeding compounds, chemosterilants, hormones, growth inhibitors, etc.

The amount of 1-substituted azacycloheptan-2-one which may be used in the present invention is an amount effective for enhancing the delivery of a pesticide to a plant pest. In the case of indirect application of the active materials to a plant, the enhanced delivery achieved through the use of the 1-substituted azacycloheptan-2-one includes improved substantivity and systemic effects of the pesticide. Generally, an effective amount ranges between about 0.01 to about 99.9 and preferably about 0.1 to 10 percent by weight of the pesticide composition.

Suitable pesticides include botanical insecticides such as, for example, nicotine, derris (rotenone) and pyrethrum; synthetic insecticides including dinitrophenols, such as, for example, DNOC; organic thiocyanates such as, for example, lethane and thanite; organochlorine insecticides including DDT and related compounds; hexachlorocyclohexane; insecticides containing the cyclodiene group such as, for example, aldrin and dieldren; organophosphorous insecticides including malathion, mevinphos, rogar, dimethoate, nenozan, miral, diazinon, dursbon, bayrusil; organocarbonate insecticides including pirimicarb, carbaryl, baygon, propoxur, zectron, carbofuran, aldicarb (Temik), methomul (Lonnate); fungicides including phenylmercury compounds, naban, metham sodium, thiron; compounds containing the n-trichloromethylthio group, such as, for example, captan, folpet and oifolatan; dinitrophenols, including dinocap (Karathane); chlorobenzynes and related compounds, quinones such as, for example, dodine and roural, sulphonamides; benzimidazoles; thiophonates; oxathinns; pyrimadines; piperozine, morpholine and azepine derrivatives; organophosphorous compounds including wepsyn, kitazin and conen, herbicides including carboxylic acid herbicides, such as, for example, 2,4-D MCPA, 2,3,6-TBA, IAA, picloram and dichlobenil; chloroaliphatic acids such as dalapan and TCA, and heterocyclic compounds such as atrozine (Gesaprim); triazales sich as amitrole, pyrazon, bromacil, endothal; bipyridinum herbicides including paraquat and diquat; benzonitriles; diphenyl ethers; organophosphorous compounds such as, for example, phosphorothiolates such as bensullide; phosphoramidates such as DMPA (Zytron); phosphonates such as glyphosate; plant growth regulators; fumigants; rodenticides including anticoagulants such as warfarin, pidone and norbormide (Raticote); sleep inducing narcotic drugs such as chloralose; gophacide, silatrane and crimidine; nematicides such as dazomet and nellite; moluscicides such as metaldehyde, methiocasb and frescon; repellants, antifeeding compounds such as ZIP; chemosterilants, hormones and growth inhibitors. Further examples of pesticides suitable for use in the present invention are known in the art (see, for example, R. Cremlyn, *Pesticides, Preparation and mode of action*, John Wiley and Sons, 1979; F. McEwan et al., *The Use and Significance of Pesticides in the Environment*, John Wiley and Sons, 1979; D. Roberts, *Fundamentals of Plant-Pest Control*, E. H. Freeman and Company, 1978.

The method of application of the pesticide composition described herein is conventional. See, for example, G. Hartley et al. *Chemicals for Pest Control*, Chapter 15, "Application of Pesticides," Pergamon Press, 1969.

The precise amount of the pesticide composition to be delivered to the plant or pest will obviously be an effective amount for the desired result expected therefrom. Most modern pesticides are used in agriculture at a dosage of less than one pound per acre. This, of course, will be ascertained by the ordinary skill of the practitioner. Due to enhanced activity which is achieved, the dosage of agent may often be decreased from that generally applicable. In accordance with the usual prudent formulating practices, a dosage near the lower end of the useful range of the particular agent may be employed initially and the dosage increased as indicated from the observed response.

The examples which follow illustrate the vehicles which may be used in carrying out the method of the present invention. Temperatures are given in degrees Centigrade. All reactions involving sodium hydride were carried out in an inert nitrogen atmosphere.

EXAMPLE 1

Preparation of 1-n-Hexylazacyclopentan-2-one having the following structure:

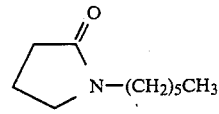

13.7 g of 50% sodium hydride-mineral oil dispersion (6.85 g NaH, 0.285M) was placed in a 1 liter flask equipped with an addition funnel, condenser and a mechanical stirrer. This was washed with 2×100 ml of petroleum ether and the petroleum ether was decanted. About 250 ml of dry toluene was then added and to this stirred mixture was added dropwise a solution of 20.35 g (0.239M) of azacyclopentane-2-one in 100 ml of dry toluene. Upon completion of addition the mixture was heated to reflux for 1 hour and then cooled to room temperature. A solution of 43.6 g (0.264M) of 1-bromohexane in 100 ml of dry toluene was added dropwise for a period of one-half hour and thereafter the mixture was refluxed for 48 hours. After cooling to room temperature, the reaction mixture was filtered and the filter cake was washed with dry toluene. The combined filtrate was concentrated to a yellow oil. Distillation gave 25.7 g (63.5%) of colorless 1-n-Hexylazacyclopentan-2-one, boiling point 98°–102°/0.5 mm.

EXAMPLE 2

Preparation of 1-n-Heptylazacyclopentan-2-one having the formula:

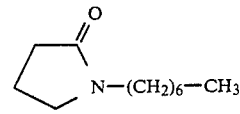

Following Example 1, on refluxing 13 g of 50% oil dispersion of sodium hydride (6.5 g NaH, 0.271M), 20.35 g (0.239M) of azacyclopentan-2-one and 47.28 g (0.264M) of 1-bromoheptan in dry toluene for 21 hours was obtained 13.6 g (31%) of colorless oil; boiling point 115°–120°/0.6 mm.

EXAMPLE 3

Preparation of 1-n-octylazacyclopentan-2-one

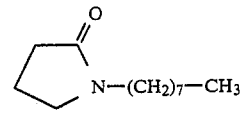

Following Example 1, from 5.44 g of 57% oil dispersion of sodium hydride (3.10 g NaH, 0.13M), 10 g (0.1174M) of azacyclopentan-2-one and 25.1 g (0.13M) of 1-bromooctane was obtained 13.6 g (59%) of colorless 1-n-nonylazacyclopentan-2-one. B.P. 123°–132°/0.3 mm.

EXAMPLE 4

Preparation of 1-n-nonylazacyclopentan-2-one having the formula:

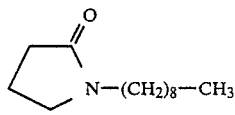

Following Example 1, from 5.44 g of 57% sodium hydride-mineral oil dispersion (3.10 g NaH, 0.13M) 10 g (0.1174M) of azacyclopentan-2-one and 27 g (0.13M) of 1-bromononane was obtained 13.4 g (56%) of 1-n-nonylazacyclopentan-2-one, b.p. 139°–143°/0.5 mm.

EXAMPLE 5

Preparation of 1-n-decylazacyclopentan-2-one having the formula:

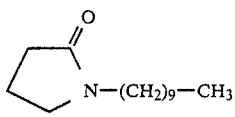

18.8 g (0.22M) of butyrolactone and 34.6 g (0.22M) of n-decylamine were mixed and heated to 180° in a round bottom flask equipped with a condenser and a Dean-Stark trap for 22 hours. The dark brown reaction mixture was distilled at reduced pressure to yield 40.9 g (82.5%) of colorless product; b.p. 150°–155°/0.5–1 mm.

EXAMPLE 6

Preparation of 1-n-dodecylazacyclopentan-2-one having the formula:

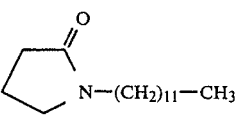

Following Example 5, 18.8 g (0.22M) of butyrolactone and 37 g (0.2M) of n-dodecylamine was heated for 24 hours. Distillation of the residue gave 40.7 g (80.3%) of 1-n-dodecylazacyclopentan-2-one; b.p. 165°–170°/0.5 mm.

EXAMPLE 7

Preparation of 1-methylazacycloheptan-2-one having the formula:

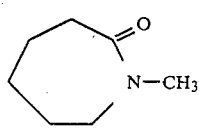

A suspension of 8.42 g of 57% sodium hydride-mineral oil suspension (4.8 g NaH, 0.2M) was washed with 2×400 ml portions of dry toluene and the toluene washings were decanted. 350 ml of dry toluene was added and the suspension was mechanically stirred while a solution of 20 g (0.177M) of azacycloheptan-2-one in 50 ml of dry toluene was added dropwise over 1 hour. After the addition was over, the mixture was refluxed for 1 hour and then cooled to room temperature. 22.0 g (0.2M) of methyl mesylate was added dropwise over 1 hour and the reaction mixture was then warmed to 50° for 1 hour. The mixture was cooled, filtered and the filter cake was resuspended in 100 ml of dry toluene and filtered. This combined to yield 20 g (88.85%) of 1-methylazacycloheptan-2-one; b.p. 85°–87°/0.1 mm.

EXAMPLE 8

Preparation of 1-n-propylazacycloheptan-2-one having the formula:

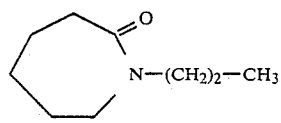

In a 1 liter 3-neck flask equipped with a dry ice/isopropanol condenser, an addition funnel and a mechanical stirrer was placed 10.2 g of 50% sodium hydride-mineral oil dispersion (5.1 g NaH, 0.2125M) and 150 ml of petroleum ether. The suspension was momentarily stirred and then sodium hydride was allowed to settle. Most of the petroleum ether was pipetted out and 200 ml of dry toluene was added. To this was added dropwise a solution of 20 g (0.177M) of azacycloheptan-2-one in 100 ml of dry toluene. The mixture was refluxed for 1 hour and then cooled to room temperature. A solution of 30.75 g (0.25M) of 1-bromopropane in 100 ml of dry toluene was added dropwise under stirring. Upon completion of the addition, the mixture was warmed to 80°–100° and the temperature was maintained there for 4 hours. Then the isopropanol-dry ice condenser was replaced with a water condenser and the reaction mixture was heated to reflux for 15 hours. The reaction mixture was cooled, filtered and the filtrate was concentrated to a yellow oil. Distillation afforded 22.2 g (81%) of colorless product; b.p. 83°–86°/0.25 mm.

EXAMPLE 9

Preparation of 1-n-butylazacycloheptan-2-one having the formula:

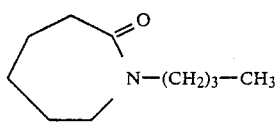

Following Example 8, from 12.75 g of 50% sodium hydride-mineral oil dispersion (6.375 g NaH, 0.266M), 25 g (0.221M) of azacycloheptan-2-one and 34.25 g (0.25M) of 1-bromobutane was obtained on 18 hour reflux 26.8 g (72%) of colorless product; b.p. 95°–100°/0.3 mm.

EXAMPLE 10

Preparation of 1-n-pentylazacycloheptan-2-one having the formula:

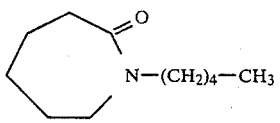

Following Example 8 and using water condenser from the start of the reaction, 10 g of 50% sodium hydride-mineral oil dispersion (5 g NaH, 0.21M), 20 g (0.177M) of azacycloheptan-2-one and 30.2 g (0.2M) of 1-bromopentane on 18 hour reflux gave 23.3 g (87%) of colorless product; b.p. 110°–115°/0.3 mm.

EXAMPLE 11

Preparation of 1-n-hexylazacycloheptan-2-one having the formula:

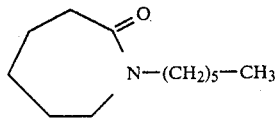

Following Example 10, from 10.2 g of 50% sodium hydride-mineral oil dispersion (5.1 g NaH, 0.2125M), 20 g (0.177M) of azacycloheptan-2-one and 33 g (0.2M) of 1-bromohexane on 19 hour reflux was obtaned 29.8 g (85.3%) of colorless product; b.p. 122°–128°/0.4 mm.

EXAMPLE 12

Preparation of 1-n-heptylazacycloheptan-2-one having the formula:

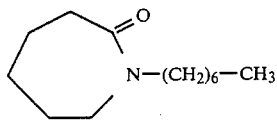

Following Example 10, 10.2 g of 50% sodium hydride-mineral oil dispersion (5.1 g of NaH, 0.2125M), 20 g (0.177M) of azacycloheptan-2-one and 35.8 g (0.2M) of 1-bromoheptane on 18 hour reflux gave 33.5 g (90%) of colorless product; b.p. 155°–158°/0/5 mm.

EXAMPLE 13

Preparation of 1-n-octylazacycloheptan-2-one having the formula:

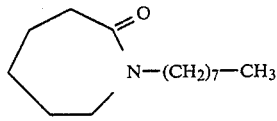

Following Example 5, heating 17.5 g (0.153M) of 6-hexanolactone and 22 g (0.17M) of 1-aminooctane at 180° for 29 hours gave 8.8 g (27%) of product; b.p. 155°–160°/0.5 mm.

EXAMPLE 14

Preparation of 1-n-nonylazacycloheptan-2-one having the formula:

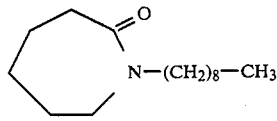

Following Example 5, heating 22.83 g (0.2M) of 6-hexanolactone and 28.65 g (0.2M) of 1-aminononane at 180° for 20 hours gave 11.5 g (26%) of product; b.p. 155°–165°/0.6 mm.

(Higher yields of 1-n-octyl- and 1-n-nonylazacycloheptan-2-one may be obtained by use of the sodium hydride method or by carrying out the reaction in a stainless steel bomb under pressure.)

EXAMPLE 15

Preparation of 1-n-decylazacycloheptan-2-one having the formula:

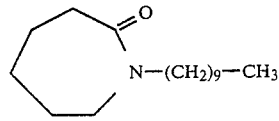

Following Example 10, 10.2 g of 50% sodium hydride-mineral oil dispersion (5.1 g NaH, 0.2125M), 20 g (0.177M) of azacycloheptan-2-one and 44.2 g (0.2M) of 1-bromodecane on 19 hours reflux gave 38 g (84.7%) of product; b.p. 158°–163°/0.25–0.3 mm.

EXAMPLE 16

Preparation of 1-n-dodecylazacycloheptan-2-one having the formula:

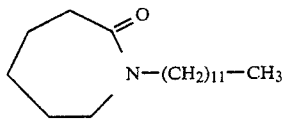

Following Example 10, 15.3 g of 50% sodium hydride-mineral oil dispersion (7.65 g NaH, 0.319M), 30 g (0.266M) of azacycloheptan-2-one and 66.1 g (0.265M) of 1-bromododecane on 20 hours reflux gave 60 g (80%) of colorless product; b.p. 175°–180°/0.3 mm.

EXAMPLE 17

Preparation of 1-n-butylazacyclononan-2-one having the formula:

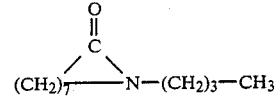

Following Example 10, 16.32 g of 50% sodium hydride-mineral oil dispersion (8.16 g NaH, 0.34M), 40 g (0.283M) of azacyclononan-2-one and 43 g (0.311M) of 1-bromobutane was refluxed for 22 hours. The reaction mixture was diluted with benzene-tolune and was extracted with water. The organic phase was separated, dried and concentrated to a yellow oil. Distillation afforded 41.4 g (74%) of product; b.p. 166°–170°/0.2 mm.

EXAMPLE 18

Preparation of 1-n-octylazacyclononan-2-one having the formula:

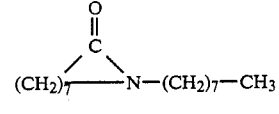

Following Example 17, 4.2 g of 50% sodium hydride-mineral oil dispersion (2.1 g NaH, 0.0875M), 10 g (0.0708M) of azacyclononan-2-one and 15 g (0.0777M)

of 1-bromooctane gave 12.5 g (70%) of product; b.p. 150°-160°/0.5 mm.

EXAMPLE 19

Preparation of 1-phenylazacyclopentan-2-one having the formula:

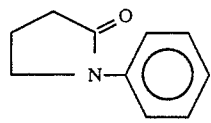

9.3 g (0.1M) of aniline and 9.5 g (0.11M) of butyrolactone were mixed and heated to 200° for 48 hours. At the end of the reaction, unreacted starting materials and water were removed at reduced pressure. Distillation of the residue gave 6.3 g (39%) of the product (89% yield based on reclaimed aniline); b.p. 138°-140° 0.3 mm. Yield in this reaction can be improved if the water formed during the reaction is separated out with or without the use of a solvent (benzene or toluene) or by carrying out the reaction under pressure.

EXAMPLE 20

Preparation of 1-benzylazacyclopentan-2-one having the formula:

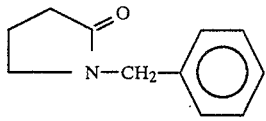

6.97 g (0.06M) of butyrolactone is mixed with 6.97 g (0.065M) of benzylamine and heated at 190° for 24 hours. Excess benzyl amine and water was distilled off and the residue was distilled to obtain 7.4 g (70%); b.p. 125°-130°/1 mm.

EXAMPLE 21

Preparation of 1-(2-chlorophenyl)azacyclopentan-2-one having the formula:

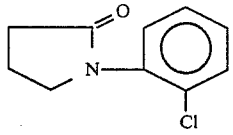

Following Example 19, 12.57 g (0.1M) of 2-chloroaniline and 9.5 g (0.11M) of butyrolactone were heated for 48 hours. The excess staging materials were removed at 50°-80°/0.3 mm. Distillation of the residue gave 4.9 g (25%) of product (45% based on recovered 2-chloroaniline); b.p. 150°-155°/0.3-0.4 mm.

EXAMPLE 22

Preparation of 1,3-Bis(1-azacyclopentan-2-onyl)propane having the formula:

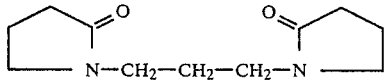

To 11.0 g of 57% sodium hydride-mineral oil suspension (6.27 g NaH, 0.261M) was added 150 ml of dry toluene and this was stirred for a few minutes. Toluene was decanted and 150 ml of fresh dry toluene was added. 20 g (0.235M) of azacyclopentan-2-one was added dropwise over 1 hour and after the addition was over the mixture was refluxed for 1 hour. 22.3 g (0.11M) of 1,3-dibromopropane was added dropwise over three hours. The refluxing was continued for 72 hours and then the reaction mixture was cooled and filtered twice, the second time through celite. The filtrate was concentrated and the residue was distilled to obtain 8.2 g (35.4%) of product; b.p. 179°-180°/0.03 mm.

EXAMPLE 23

Preparation of 1,6-Bis-(1-azacyclopentan-2-onyl)hexane having the formula:

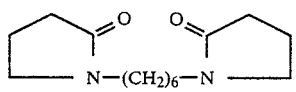

11.62 g (0.1M) of 1,6-diaminohexane and 21.66 g (0.25M) of butyrolactone were mixed and heated to 150°-165° for 22 hours. Excess butyrolactone was then distilled off at reduced pressure (80°/2 mm). The light brown residue was poured into a crystallization dish where it immediately solidified. The solid was taken in chloroform, powdered, filtered and the tan powder was washed with chloroform.

Yield 22.0 g (87%); melting point 101°-103°.

I claim:

1. An improved method for plant pest control, comprising the steps of:
   delivering, as a first ingredient, an effective amount of a plant pesticide to a plant; and
   enhancing penetration of the plant pesticide into a target organism associated with the plant, namely a plant, an insect, a fungus, a mollusk, an arachnid, or a nematode, by simultaneously delivering, as a different, second ingredient, a penetration enhancing amount of a compound of the formula:

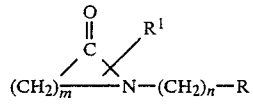

where $R^1$ is H or a lower alkyl having 1-4 carbon atoms, m is 5-7, n is 6-17, and R is —$CH_3$ or

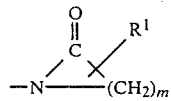

2. The method of claim 1, wherein $R^1$ is H, and R is —$CH_3$.

3. The method of claim 2, in which the target organism is a plant.

4. The method of claim 2, in which the target organism is an insect.

5. The method of claim 2, in which the target organism is an arachnid.

6. The method of claim 2, in which the target organism is a mollusk.

7. The method of claim 2, in which the target organism is a nematode.

8. The method of claim 2, in which the target organism is a fungus.

9. The method of claim 1, wherein the second ingredient is 1-n-dodecylazacycloheptan-2-one.

10. The method of claim 9, in which the target organism is a plant.

11. The method of claim 9, in which the target organism is an insect.

12. The method of claim 9, in which the target organism is an arachnid.

13. The method of claim 9, in which the target organism is a mollusk.

14. The method of claim 9, in which the target organism is a nematode.

15. The method of claim 9, in which the target organism is a fungus.

* * * * *